(12) United States Patent
Lanius et al.

(10) Patent No.: US 11,475,302 B2
(45) Date of Patent: Oct. 18, 2022

(54) MULTILAYER PERCEPTRON BASED NETWORK TO IDENTIFY BASELINE ILLNESS RISK

(71) Applicant: KONINKLIJKE PHILIPS N.V., Eindhoven (NL)

(72) Inventors: Stephanie Lanius, Cambridge, MA (US); Erina Ghosh, Boston, MA (US); Emma Holdrich Schwager, Englewood, CO (US); Larry James Eshelman, Ossining, NY (US)

(73) Assignee: Koninklijke Philips N.V., Eindhoven (NL)

( * ) Notice: Subject to any disclaimer, the term of this patent is extended or adjusted under 35 U.S.C. 154(b) by 373 days.

(21) Appl. No.: 16/840,856

(22) Filed: Apr. 6, 2020

(65) Prior Publication Data
US 2020/0320391 A1   Oct. 8, 2020

Related U.S. Application Data

(60) Provisional application No. 62/829,683, filed on Apr. 5, 2019.

(51) Int. Cl.
*G06N 3/08* (2006.01)
*G06N 3/04* (2006.01)
(Continued)

(52) U.S. Cl.
CPC .............. *G06N 3/08* (2013.01); *A61B 5/201* (2013.01); *G06K 9/6261* (2013.01);
(Continued)

(58) Field of Classification Search
CPC ........ G06N 3/08; G06N 3/0481; G06N 20/00; A61B 5/201; A61B 5/7267; A61B 5/7275;
(Continued)

(56) References Cited

U.S. PATENT DOCUMENTS 8,990,135 B2 * 3/2015 Syed .................. G16H 50/30
706/924
2017/0017899 A1 * 1/2017 Maor .................. G06F 16/285
(Continued)

OTHER PUBLICATIONS

Mehta, RL et al. "Acute Kidney Injury Network: report of an initiative to improve outcomes in acute kidney injury". Critical Care (2007)11(2):R31.
(Continued)

*Primary Examiner* — Dhaval V Patel

(57) ABSTRACT

A method for training a baseline risk model, including: pre-processing input data by normalizing continuous variable inputs and producing one-hot input features for categorical variables; providing definitions for clean input data and dirty input data based upon various input data related to a patient condition; segmenting the input data into clean input data and dirty input data, wherein the clean input data includes a first subset and a second subset, where the first subset and the second subset include all of the clean input data and are disjoint; training a machine learning model using the first subset of the clean data; and evaluating the performance of the trained machine learning model using the second subset of the clean input data and the dirty input data.

24 Claims, 2 Drawing Sheets

(51) Int. Cl.
    *G06N 20/00*   (2019.01)
    *A61B 5/20*    (2006.01)
    *G06K 9/62*    (2022.01)
    *G16H 50/30*   (2018.01)

(52) U.S. Cl.
    CPC ......... *G06K 9/6262* (2013.01); *G06N 3/0481* (2013.01); *G06N 20/00* (2019.01); *G16H 50/30* (2018.01)

(58) Field of Classification Search
    CPC .... G06K 9/6261; G06K 9/6262; G16H 50/30; G16H 50/70
    See application file for complete search history.

(56) References Cited

U.S. PATENT DOCUMENTS

| 2018/0315182 | A1* | 11/2018 | Rapaka | G16H 50/70 |
| 2020/0005901 | A1* | 1/2020 | Cohen | G16B 20/00 |
| 2020/0303075 | A1* | 9/2020 | Krishna | G16H 50/30 |

OTHER PUBLICATIONS

KDIGO AKI Work Group. (2012) "KDIGO clinical practice guideline for acute kidney injury". Kidney Int Suppl 2 (a):1-138.
Di Noia, T. et al., "An end stage kidney disease predictor based on an artificial neural networks ensemble". Expert Systems with Applications 40 (2013) 4438-4445.
Correia, C. "Data-based modelling for the prediction of mortality in acute kidney injury patients". Instituto Superior Tecnico, Lisbon, Portugal (2017).
Adhikari, L. et al., "Improved predictive models for acute kidney injury with IDEAs: Intraoperative data embedded analytics". Plos one (2019).
Ismail, A.R. et al., "Early prediction of acute kidney injury using machine learning algorithms". Canadian Society of Nephrology. Jun. 8, 2018. https://doi.org/10.1177/2054358118776326.
Cruz, H. et al., "Early detection of acute kidney injury with Bayesian networks". SMBM (2016).

* cited by examiner

MULTILAYER PERCEPTRON BASED NETWORK TO IDENTIFY BASELINE ILLNESS RISK

TECHNICAL FIELD

Various exemplary embodiments disclosed herein relate generally to a multilayer perceptron based network to identify baseline illness risk.

BACKGROUND

Various illnesses affect patients and identifying the baseline illness risk for these patients provides a medical caregiver important information in identifying, diagnosing, and treating such illnesses, especially illnesses that may be secondary illnesses and illnesses that may be non-symptomatic in their early stages. One example of such a disease is acute kidney injury (AKI) that commonly affects critically ill patients as a secondary condition during their ICU stay. AKI adversely affects patient outcomes such as mortality, ICU and hospital length of stay, and post-discharge quality of life, and AKI increases the financial burden on hospitals and patients. Because AKI is a secondary condition and is non-symptomatic in the initial stages, it is often under-diagnosed and only identified when a severe kidney injury occurs. However, early detection of kidney injury can lead to preventative measures being taken which would impede the progression of the disease. Likewise, the early detection of other illnesses would provide a great benefit to the patients and to the healthcare system in general, as early detection of illnesses prevents more acute illnesses from occurring, which allows for a better use of scarce medical resources to be used to treat more patients and/or to reduce costs associated with these diseases.

Kidney injury detection may be done using urine output and creatinine values according to various known methods such as those disclosed in: Mehta, R L et al. (2007) Acute Kidney Injury Network: report of an initiative to improve outcomes in acute kidney injury, Critical Care 11:R31; and KDIGO AKI Work Group (2012) KDIGO clinical practice guideline for acute kidney injury, Kidney Int Suppl 2(1):1-138. These criteria inform the clinician when kidney injury has already occurred.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method for training a baseline risk model, including: pre-processing input data by normalizing continuous variable inputs and producing one-hot input features for categorical variable inputs; providing definitions for clean input data and dirty input data based upon various input data related to a patient condition; segmenting the input data into clean input data and dirty input data, wherein the clean input data includes a first subset and a second subset, where the first subset and the second subset include all of the clean input data and are disjoint; training a machine learning model using the first subset of the clean data; and evaluating the performance of the trained machine learning model using the second subset of the clean input data and the dirty input data.

Various embodiments are described, wherein the machine learning model is a neural network.

Various embodiments are described, wherein the machine learning model includes two hidden layers.

Various embodiments are described, wherein the baseline risk is the risk of acute kidney injury.

Various embodiments are described, wherein the various input data related to a patient condition includes a maximum creatinine stage and a maximum urine stage.

Various embodiments are described, wherein clean data includes patient data where the maximum creatinine stage=0 and the maximum urine stage=0 or the maximum creatinine stage>1 and the maximum urine stage>1.

Various embodiments are described, wherein the nodes of the first hidden layer and the second hidden layer include rectifier linear units.

Various embodiments are described, wherein the linear rectifier units have a negative slope.

Various embodiments are described, further comprising applying a sigmoid function to an output layer of the neural network.

Various embodiments are described, wherein the loss function used to train the neural network is a binary cross entropy loss function.

Various embodiments are described, wherein pre-processing input data further includes applying a prevalence threshold to binary input data.

Various embodiments are described, wherein pre-processing input data further includes using a word embedding which maps high-cardinality categorical features into a lower dimensional space to categorical input data.

Further various embodiments relate to a non-transitory machine-readable storage medium encoded with instructions for training a baseline risk model, including: instructions for pre-processing input data by normalizing continuous variable inputs and producing one-hot input features for categorical variables; instructions for providing definitions for clean input data and dirty input data based upon various input data related to a patient condition; instructions for segmenting the input data into clean input data and dirty input data, wherein the clean input data includes a first subset and a second subset, where the first subset and the second subset include all of the clean input data and are disjoint; instructions for training a machine learning model using the first subset of the clean data; and instructions for evaluating the performance of the trained machine learning model using the second subset of the clean input data and the dirty input data.

Various embodiments are described, wherein the machine learning model is a neural network.

Various embodiments are described, wherein the machine learning model includes two hidden layers.

Various embodiments are described, wherein the baseline risk is the risk of acute kidney injury.

Various embodiments are described, wherein the various input data related to a patient condition includes a maximum creatinine stage and a maximum urine stage.

Various embodiments are described, wherein clean data includes patient data where the maximum creatinine stage=0 and the maximum urine stage=0 or the maximum creatinine stage>1 and the maximum urine stage>1.

Various embodiments are described, wherein the nodes of the first hidden layer and the second hidden layer include rectifier linear units.

Various embodiments are described, wherein the linear rectifier units have a negative slope.

Various embodiments are described, further comprising instructions for applying a sigmoid function to an output layer of the neural network.

Various embodiments are described, wherein the loss function used to train the neural network is a binary cross entropy loss function.

Various embodiments are described, wherein pre-processing input data further includes applying a prevalence threshold to binary input data.

Various embodiments are described, wherein pre-processing input data further includes using a word embedding which maps high-cardinality categorical features into a lower dimensional space to categorical input data.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

Figure 1:
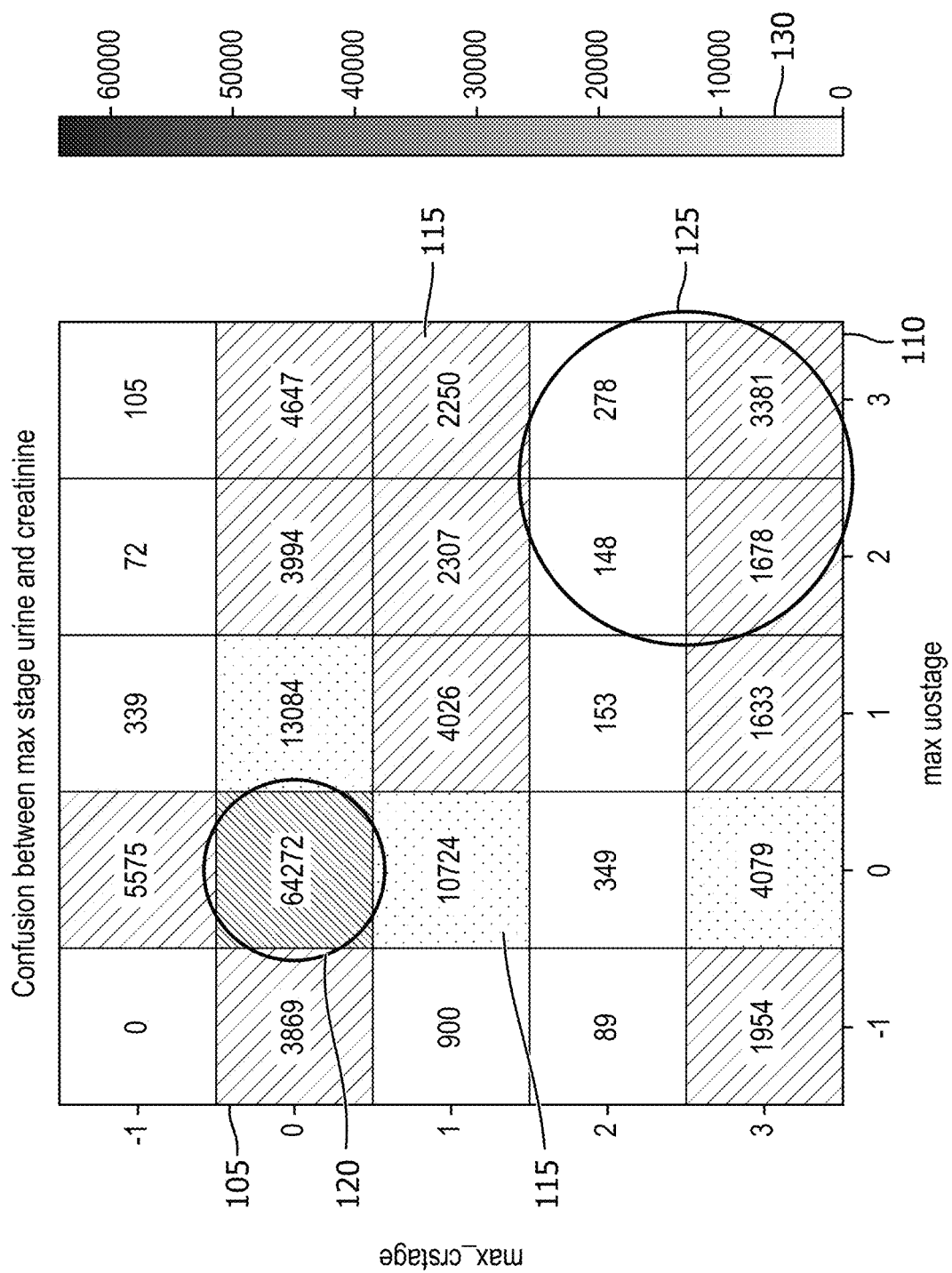
FIG. 1 is a graphical table showing the number of patients with different maximum creatinine stage and maximum urine stage values.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Baseline risk models may be developed and used to evaluate risk of patients developing a specific condition. These models often lack generalizability. In this disclosure, a machine learning algorithm to predict patient's risk of developing acute kidney injury (AKI), for example, at admission to the intensive care unit (ICU). The model described herein is easy to use and may potentially be applied to many applications and deals very well with different data types. Pre-processing of the input data results in a dataset that is easy to use. The structure of the multilayer perceptron network is made to be robust. Therefore, the multi-layer perceptron network implementation may identify a precise, continuous risk for a specific binary disease without needing much adaption for one prediction task.

The model for predicting baseline AKI risk described herein allows clinicians to proactively reduce the risk of developing AKI by monitoring fluid status and not prescribe nephrotoxic drugs. An additional benefit of predicting increased AKI risk is that clinicians can carefully monitor such patients and identify AKI quickly. As this model may be applied to other conditions as well, other benefits of early detection of those conditions will result as well.

Previously, researchers have tried to build AKI prediction models. These models use a mixture of demographic data and ICU data to predict the AKI risk. The models try to predict the AKI stage based on creatinine values only. The drawback of this approach is that it ignores the AKI risk due to low urine output. Urine output is an earlier indicator of AKI, however, urine output data is often incompletely charted and consequently noisy. The creatinine data is reliable, but elevated creatinine is a late marker for kidney injury, meaning that once the elevated creatine is detected kidney injury may have already begun.

Therefore, an easy-to-use model that can access multiple disease risks at admission would be highly valuable. Often, machine learning models for risk assessment are adapted carefully for the specific prediction task and the dataset associated with the specific prediction task that hinders the transfer of knowledge to another prediction tasks. This is highly impractical, as many models will generalize poorly. The model described herein is easily adaptable to specific tasks, and because of the robust network structure chosen as well as the robust implementation, the model overcomes the shortcomings of most neural network implementations.

In the embodiments described herein, pre-processing of binary data is not necessary and continuous features are standardized as described below. Further, categorical features are one-hot encoded, which means that for every value in a categorical feature, a new feature is created where the value of that feature is 1 only when that categorical feature as the specified value, and 0 otherwise.

The baseline risk model includes the following features. The first feature is a framework to process different types of features in a generalizable manner. The second feature prevents learning false structures in the data, by splitting the input data into clean and dirty samples. Clean samples are then used for training and testing, while dirty samples are only used for testing. Splitting the data in this way results in overall improved outcome when a compelling split is applied.

The model structure is characterized by two goals: robust algorithms, which prevent gradients from being zero; and high-speed convergence.

Pre-processing of the input data is largely dependent on the input data type. The input features may be divided into three types: continuous features; categorical features, and binary features.

Continuous features (such as age, weight, height, body mass index (BMI), or Charlson index) are standardized by calculating the z-score as follows:

$$Z = \frac{x - \mu}{\sigma},$$

where x is the input value feature, $\mu$ is the mean value of the feature across the input data, and $\sigma$ is the standard deviation of the feature across the input data. This normalization allows for the various input features to have the same relative values about their mean and standard deviation in order to prevent a feature with larger numerical values from dominating features with a smaller numerical value.

Categorical features (such as gender, race, admitting source, service code, type of surgery, etc.) are features that have a finite number of different values which are known beforehand (e.g. female and male for gender; or emergency, elective or none for type of surgery). These categorical features provide increased ability to differentiate patients from one another. Hence, they help in determining the baseline risk of the patients. Categorical features are one-hot encoded. For every value of the categorical feature (e.g., three different values for type of surgery), a new feature is defined which may be thought of as a column in the input data matrix. The values for each hot feature are binary and indicate if the value of feature was equal to that value associated with the feature. As only one value can be set for each one-hot feature, only one of the one-hot features associated with the categorical feature will contain a one for that specific patient, and all of the others will be set to zero. Therefore, it is called one-hot encoding, as for example with three surgical categories, two columns will contain a zero while one will contain a one. For example, a female patient without surgery will have the following encoding using the following one-hot encoding definitions:

Gender_female, gender_male: [1, 0];

Surgery_emergency, surgery_elective, surgery_none: [0, 0, 1].

Binary features (such as specific co-morbidities like whether the patient has diabetes or not) do not need specific pre-processing. However, many of these features have very low prevalence, being measured only in a small proportion of the population. Therefore, prevalence thresholds may be placed on the binary features to prevent the model from overfitting and unnecessarily increasing the dimensionality. In the examples shown herein, the prevalence threshold is set to be 0.5%. An alternative to using a prevalence threshold, includes using a word embedding which maps high-cardinality categorical features into a lower dimensional space. This method, however, is not necessary to obtain good results, and either approach may be used, or other approaches to compensate for the model overfitting on features that have a low prevalence in the patient population.

FIG. 1 is a graphical table showing the number of patients with different maximum creatinine stage and maximum urine stage values. Both the maximum creatinine stage and maximum urine stage are coded to values of −1, 0, 1, 2, or 3. The input samples may be divided into clean and noisy samples. Clean samples mean samples that clearly indicate the presence or absence of kidney problems. This is based upon the kidney disease improving global outcomes (KDIGO) criteria (which provide clinical guidelines for AKI that build off of the RIFLE (risk, injury, failure, loss of kidney function) criteria and the AKIN (Acute Kidney Injury Network) criteria) to divide patients into clean and dirty groups. In this example, clean patients have either max_creatinine stage=0 and max urine stage=0 or creatinine>1 and urine>1. The other values present less of a clear indication of the presence or absence of AKI, and hence are considered dirty. Patients who do not have enough data to label one of values (i.e., maximum creatinine stage and maximum urine stage) are included in the noisy cohort and may be given a value of −1. FIG. 1 shows the grouping of patients using data from a database of patients available to the inventors. The horizontal axis 105 is the AKI stage using urine output, and the vertical axis 110 is the AKI stage using creatinine. The numbers in each block 115 correspond to specific values representing the number of patients in the database who meet this criterion. Patients within the circles 120 and 125 are in the clean cohort, all other patients are within the noisy cohort. Stage −1 indicates that there was not enough data to label a data sample. While this specific example of defining clean and dirty samples is disclosed, other methods of defining clean and dirty samples may be developed for AKI and other conditions that may be modeled as well.

This method of segmenting the data input into the baseline risk model provides better results than using all samples both for training and for testing. However, over-selecting the clean samples may result in a reduction in performance. Based upon experiments, a primary result is that it seems valuable to have at least 50% of the samples in the clean dataset. The baseline risk model is then trained on the clean data samples, and the performance of the baseline risk model is evaluated using both a held-out clean dataset as well as on the dirty data samples.

Intuitively, dividing the patients into clean and noisy makes sense. Patients with low prevalence of data or medically ambiguous criteria are difficult to interpret. For instance, a patient which only stayed 6 hours in ICU may be rather healthy and have been discharged early. However, really sick patients may stay only 6 hours in ICU and then die. Both will have a very low prevalence of data due to their short length of stay, but in fact those two patients belong to two very distinctive cohorts.

Figure 2:
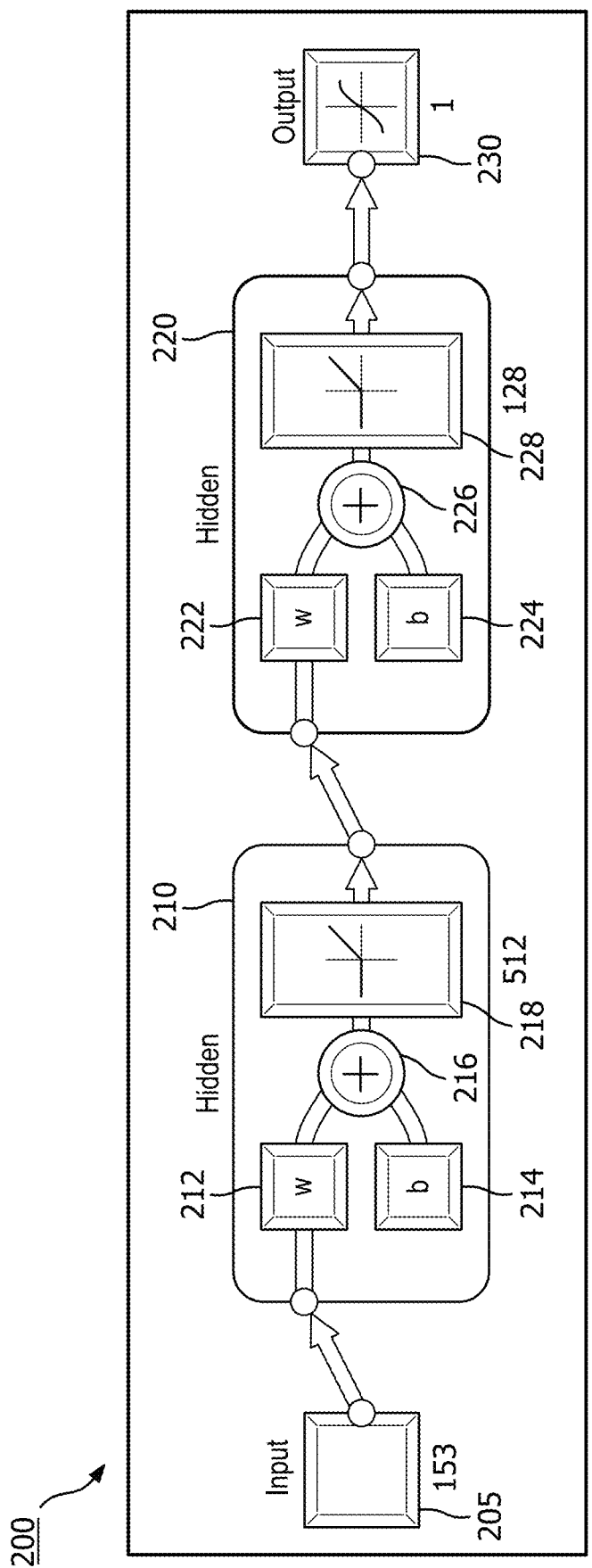
FIG. 2 illustrates a neural network implementation of the baseline risk model.

FIG. 2 illustrates a neural network implementation of the baseline risk model. The neural network 200 includes an input layer 205, a first hidden layer 210, a second hidden layer 220, and an output layer 230. In this example, the input layer includes 153 inputs. The first hidden layer 210 includes 512 nodes that are each connected to the 153 inputs. Each node of the first hidden layer 210 includes a weight 212 and a bias 214, where the input is multiplied by the weight 212 and added to the bias 214. The output of the adder 216 is input to the activation function 218. The second hidden layer 220 includes 128 nodes that are each connected to the 512 outputs of the first hidden layer. Like the first hidden layer, each node of the second hidden layer 220 includes a weight 222 and a bias 224, where the input is multiplied by the weight 222 and added to the bias 224. The output of the adder 226 is input to the activation function 228. The 128 outputs of the second hidden layer 220 are then input to the output layer 230, which produces the baseline risk score. The activation functions may be rectifier linear units, but other activation units may be used to suit different modelling tasks.

The neural network 200 is trained using the clean samples as described above. To speed up training, small batches (for example, 4096 samples each) may be used to train the neural network model 200. This results in a quick convergence to a set of weights to be used in the neural network model during inference.

For example, the Adam optimizer with high weight decay (0.004) may be used to train the model. The Adam algorithm is a first-order gradient-based optimization of stochastic objective functions, based on adaptive estimates of lower-order moments. A strong normalization may be used, as the alternative would be to remove feature space dimensionality. Further, to speed up learning, a negative slope is chosen in the rectifier linear units, as otherwise, 0s in the data (e.g. in binary data) would result in 0 gradients.

A sigmoid function may be applied on the last layer to limit the output to the range [0, 1], which may then be interpreted as 0=very low risk of disease, 1=very high risk of disease, and 0.5=intermediate risk.

A binary cross entropy function may be used as the loss function defined as:

$$\mathcal{L}(\theta) = -\frac{1}{n}\sum_{i=1}^{n}[y_i \log(p_i) + (1-y_i)\log(1-p_i)].$$

In this case N=2 as there is only a binary label (i.e., will get disease, will not get disease). The formula then gets much simpler. It is noted that other loss functions may be used as well.

This neural network baseline risk model may be used for multiple classification tasks. It may be applied to mortality (0, 1) or to the length of stay prediction (<3 days, >3 days). The neural network baseline risk model may be implemented to provide more predictive information to clinicians.

The neural network baseline risk model solves the technological problem of determining the risk of a patient having a certain illness or condition. A specific method of preprocessing the data to encode the data using specific techniques and then identifying clean and dirty input data samples are carried out. Then a portion of the clean input data may be used to train the neural network baseline risk model, with the remaining clean data and dirty data being used to test and verify the model. Further, the use on one-hot encoding provides benefits when the input data includes categorical features.

The embodiments described herein may be implemented as software running on a processor with an associated memory and storage. The processor may be any hardware device capable of executing instructions stored in memory or storage or otherwise processing data. As such, the processor may include a microprocessor, field programmable gate array (FPGA), application-specific integrated circuit (ASIC), graphics processing units (GPU), specialized neural network processors, cloud computing systems, or other similar devices.

The memory may include various memories such as, for example L1, L2, or L3 cache or system memory. As such, the memory may include static random-access memory (SRAM), dynamic RAM (DRAM), flash memory, read only memory (ROM), or other similar memory devices.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. This software may implement the various embodiments described above.

Further such embodiments may be implemented on multiprocessor computer systems, distributed computer systems, and cloud computing systems. For example, the embodiments may be implemented as software on a server, a specific computer, on a cloud computing, or other computing platform.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for training a baseline risk model, comprising:
pre-processing input data by normalizing continuous variable inputs and producing one-hot input features for categorical variable inputs;
providing definitions for clean input data and dirty input data based upon various input data related to a patient condition;
segmenting the input data into clean input data and dirty input data, wherein the clean input data includes a first subset and a second subset, where the first subset and the second subset include all of the clean input data and are disjoint;
training a machine learning model using the first subset of the clean data; and
evaluating the performance of the trained machine learning model using the second subset of the clean input data and the dirty input data.

2. The method of claim 1, wherein the machine learning model is a neural network.

3. The method of claim 2, wherein the machine learning model includes two hidden layers.

4. The method of claim 1, wherein the baseline risk is the risk of acute kidney injury.

5. The method of claim 4, wherein the various input data related to a patient condition includes a maximum creatinine stage and a maximum urine stage.

6. The method of claim 5, wherein clean data includes patient data where the maximum creatinine stage=0 and the maximum urine stage=0 or the maximum creatinine stage>1 and the maximum urine stage>1.

7. The method of claim 3, wherein the nodes of the first hidden layer and the second hidden layer include rectifier linear units.

8. The method of claim 7, wherein the linear rectifier units have a negative slope.

9. The method of claim 3, further comprising applying a sigmoid function to an output layer of the neural network.

10. The method of claim 3, wherein the loss function used to train the neural network is a binary cross entropy loss function.

11. The method of claim 1, wherein pre-processing input data further includes applying a prevalence threshold to binary input data.

12. The method of claim 1, wherein pre-processing input data further includes using a word embedding which maps high-cardinality categorical features into a lower dimensional space to categorical input data.

13. A non-transitory machine-readable storage medium encoded with instructions for training a baseline risk model, comprising:
instructions for pre-processing input data by normalizing continuous variable inputs and producing one-hot input features for categorical variables;
instructions for providing definitions for clean input data and dirty input data based upon various input data related to a patient condition;

instructions for segmenting the input data into clean input data and dirty input data, wherein the clean input data includes a first subset and a second subset, where the first subset and the second subset include all of the clean input data and are disjoint;

instructions for training a machine learning model using the first subset of the clean data; and instructions for evaluating the performance of the trained machine learning model using the second subset of the clean input data and the dirty input data.

14. The non-transitory machine-readable storage medium of claim 13, wherein the machine learning model is a neural network.

15. The non-transitory machine-readable storage medium of claim 14, wherein the machine learning model includes two hidden layers.

16. The non-transitory machine-readable storage medium of claim 13, wherein the baseline risk is the risk of acute kidney injury.

17. The non-transitory machine-readable storage medium of claim 16, wherein the various input data related to a patient condition includes a maximum creatinine stage and a maximum urine stage.

18. The non-transitory machine-readable storage medium of claim 17, wherein clean data includes patient data where the maximum creatinine stage=0 and the maximum urine stage=0 or the maximum creatinine stage>1 and the maximum urine stage>1.

19. The non-transitory machine-readable storage medium of claim 15, wherein the nodes of the first hidden layer and the second hidden layer include rectifier linear units.

20. The non-transitory machine-readable storage medium of claim 19, wherein the linear rectifier units have a negative slope.

21. The non-transitory machine-readable storage medium of claim 15, further comprising instructions for applying a sigmoid function to an output layer of the neural network.

22. The non-transitory machine-readable storage medium of claim 15, wherein the loss function used to train the neural network is a binary cross entropy loss function.

23. The non-transitory machine-readable storage medium of claim 14, wherein pre-processing input data further includes applying a prevalence threshold to binary input data.

24. The non-transitory machine-readable storage medium of claim 14, wherein pre-processing input data further includes using a word embedding which maps high-cardinality categorical features into a lower dimensional space to categorical input data.

* * * * *